United States Patent [19]

Eikmeier et al.

[11] Patent Number: 5,188,966
[45] Date of Patent: Feb. 23, 1993

[54] TEST CARRIER WITH SEPARATION MEANS FOR ANALYZING A SAMPLE FLUID

[75] Inventors: Heino Eikmeier, Lorsch; Anselm Rothe, Birkenau, both of Fed. Rep. of Germany

[73] Assignee: Boehringer Mannheim GmbH, Mannheim, Fed. Rep. of Germany

[21] Appl. No.: 654,110

[22] Filed: Feb. 12, 1991

[30] Foreign Application Priority Data

Feb. 19, 1990 [DE] Fed. Rep. of Germany ....... 4005021

[51] Int. Cl.$^5$ ...................... G01N 21/77; G01N 31/22
[52] U.S. Cl. .................................. 436/170; 436/169; 436/164; 436/165; 422/55; 422/56; 422/58; 435/805; 435/970
[58] Field of Search ..................... 422/55, 56, 57, 58, 422/60; 436/164, 165, 169, 170; 435/805, 970; 356/244, 246

[56] References Cited

U.S. PATENT DOCUMENTS

| | | | |
|---|---|---|---|
| 3,582,537 | 6/1971 | Perreault | 139/425 R |
| 3,723,064 | 3/1973 | Liotta | |
| 4,292,272 | 9/1981 | Kitajima et al. | 422/56 X |
| 4,780,280 | 10/1988 | Berger et al. | 422/58 X |
| 4,816,224 | 3/1989 | Vogel et al. | 422/58 X |
| 4,839,297 | 6/1989 | Freitag et al. | 422/58 X |
| 4,876,067 | 10/1989 | Deneke et al. | 422/57 X |

FOREIGN PATENT DOCUMENTS

| | | |
|---|---|---|
| 0182373 | 11/1985 | European Pat. Off. |
| 0313858 | 5/1989 | European Pat. Off. |
| 3130749C2 | 6/1984 | Fed. Rep. of Germany |

Primary Examiner—Jill A. Johnston
Assistant Examiner—Maureen M. Wallenhorst
Attorney, Agent, or Firm—Nikaido, Marmelstein, Murray & Oram

[57] ABSTRACT

Test carrier for analyzing a sample fluid with several test layers which form a sample fluid transport path and contain a reagent system which reacts with the sample fluid to produce a detectable signal. The test carrier includes a reservoir layer of absorbent material, a detection layer arranged in the fluid transport path downstream the reservoir layer, in which a detectable signal is formed, and a separating layer arranged between the reservoir layer and the detection layer. The separating layer makes a two-step process possible. Fluid contact between the reservoir layer and the detection layer arises only with pressure loading of the layer assembly of the reservoir layer, separating layer and detection layer. A more uniform optical detection signal, and consequently better accuracy, can be achieved because the separating layer is made up of a hydrophilic material, wich is in the form of a lattice-shaped structure, in which the mean width of the lattice openings is more than 0.05 mm, and the threads from which the lattice-shaped structure is formed are multi-filament.

12 Claims, 1 Drawing Sheet

TEST CARRIER WITH SEPARATION MEANS FOR ANALYZING A SAMPLE FLUID

BACKGROUND OF THE INVENTION

The invention relates to a test carrier for analyzing a sample fluid having several test layers arranged on the test carrier so that they are wetted in succession by the sample fluid. The sample is placed onto one of the layers, which is referred to as the sample feeding layer. The test layers form a fluid transport path for the test carrier.

Test carriers are used for analyzing sample fluids, in particular body fluids of man or animals. They are distinguished from the previously known analytical methods using liquid reagents above all by their ease of handling. The analyses can therefore also be conducted without specialized staff and near the patient.

There is embedded in the test layers a reagent system usually consisting of several reagents, in which the reagents are dissolved by the fluid and the reaction of sample and reagents leads to a detectable signal, in particular a color change in a detection layer. The detection signal can be visually or, preferably, instrumentally evaluated. Reflection photometry is typically employed to evaluate a color change. The invention is directed in particular towards test carriers which generate an optically measurable detection signal.

One problem with the performance of complicated analyses by test carriers is that the separation in time of several reaction steps is not a simple matter. The sample fluid usually flows along the fluid transport path largely uncontrolled.

The invention is directed towards a test carrier having a two-step process cycle, made possible by means of a separating layer. Such a test carrier is described in DE-C-31 30 749. A hydrophobic net, which is arranged in the fluid transport path between the reservoir layer of absorbent material and the detection layer, is used as the separating layer. In the previously known test carrier the reservoir layer, the hydrophobic net and the detection layer simply lie above one another on a band-shaped base layer of rigid plastic foil. They are bonded at one edge to the base layer. The reservoir layer is larger than the layers superimposed on it, so that it is only partly covered by the latter. The sample fluid is placed onto the part of the reservoir layer not covered by the detection layer and spreads out in the former beneath the detection layer. The hydrophobic net ensures that the detection layer is not immediately wetted by the fluid. In this state an initial reaction step can take place, the reagents being able to be contained in the reservoir layer or in further test layers which are situated immediately in front of the reservoir layer in the fluid transport path.

The fluid barrier formed by the hydrophobic net is only overcome if a pressure perpendicular to the surface of the layers is exerted, either manually or mechanically by a corresponding component of the evaluating instrument onto the layer assembly consisting of the reservoir layer, the hydrophobic net and the detection layer. The sample fluid then wets the detection layer and, where applicable, other test layers arranged between the hydrophobic net and the detection layer, and the proper detection reaction is initiated.

The use of a hydrophobic net separating layer permits a clean separation of two reaction steps on a test carrier. It is a disadvantage, however, that the color formation in the detection layer is in many cases not sufficiently uniform. This problem can be overcome by providing a thick reservoir layer and a correspondingly large sample amount. Additionally or alternatively the structure of the detection layer can be designed to ensure good lateral spreading of the fluid or an additional spreading layer may be located between the hydrophobic net and the detection layer. These measures lead however to an increased absorption of fluid by the test carrier. This is contrary to the goal of providing test carriers with as little fluid absorption as possible, because the required amount of sample fluid and the amount of reagent required in the test carrier are thereby reduced. Moreover, the detection layer should be as thin as possible in order to ensure intensive color formation. As a rule, however, a thin detection layer has poor lateral spreading and is therefore sensitive to non-uniform color formation.

BRIEF SUMMARY OF THE INVENTION

An object of the invention is therefore to provide a test carrier having a two-step reaction cycle and which exhibits a uniform wetting of the detection layer. Another object of the invention is to provide a test carrier which requires a very small sample amount. Yet another object is to provide a test carrier having very thin layers with low fluid absorption.

In one aspect, the present invention relates to a test carrier for analysis of a sample fluid, comprising:
  i) means for receiving and storing a sample fluid;
  ii) means for generating a detection signal based on reaction of said sample fluid;
  iii) means for separating said receiving means and reaction means, comprising a plurality of hydrophilic multifilament fibers having a lattice-shaped structure, said structure having openings defined by adjacent fibers, and said openings having a fiber separation distance which is effective to prevent saturation of the openings by capillary action;
  iv) means for joining said receiving means and said generating means into fluid contact relationship such that at least a portion of said sample fluid is transported from said receiving means to said generating means;
  v) means for housing said receiving means, said generating means, said separating means and said joining means.

In a second aspect, the present invention is directed to a process for the determination of an analyte in a sample fluid, comprising
  depositing a sample fluid on a sample fluid reservoir area of a test carrier having a signal generation area containing a reactant capable of reacting with said analyte and initially separated from fluid contact relationship with said receiving area,
  placing said signal generation area into fluid contact relationship with said receiving area,
  reacting said analyte in said sample fluid with said reactant in said signal generation area to produce a detectable signal, and
  measuring said detectable signal, wherein said sample reservoir area and said signal generation area are initially separated by a plurality of hydrophilic multifilament fibers having a lattice-shaped structure, said structure having openings defined by adjacent fibers, and said openings having a fiber separation distance which is effective to prevent saturation of the openings by capillary action.

The reaction of the sample fluid which generates the detection signal, preferably the reaction between the analyte and the reactant in the signal generation area, is suitably carried out at a temperature of between 5° C. above the freezing temperature of the sample fluid and about 5° C. below the boiling temperature of the sample fluid. Preferably, the signal generating reaction is carried out at ambient temperatures.

DETAILED DESCRIPTION OF THE PREFERRED EMBODIMENT

Figure 1:
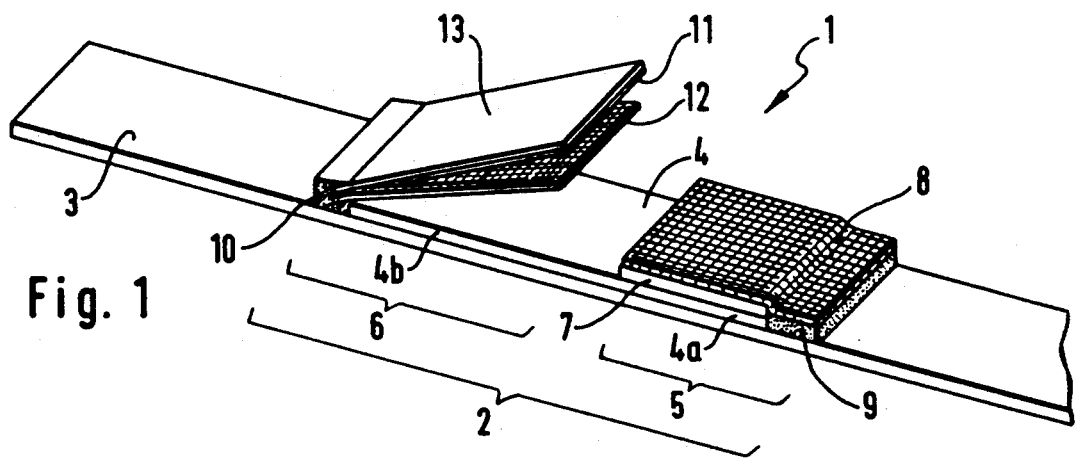
FIG. 1 is a perspective view of a test carrier according to the invention.

The objects summarized above are achieved with a test carrier characterized by the fact that
the separating layer comprises a hydrophilic material,
the separating layer has a lattice-shaped structure, in which the mean width of the lattice openings is at least approximately 0.05 mm, and
the lattice-shaped structure is formed of multi-filament threads.

Surprisingly, such a separating layer simultaneously provides a reliable separating effect and a distributing effect on the fluid, which makes uniform color formation possible.

The means for receiving and storing a sample fluid may be any absorbent material which can receive and store one or more body fluids of a mammal such as man. Preferably, the receiving means can also store at least one reagent which will be dissolved by and react with the sample fluid. The absorbent material may also be selected so that one component of the sample fluid is permanently retained by the material. For example, a glass fiber material may be selected as the absorbent material so that the red blood cells of a blood sample will be retained in order to provide pure plasma for subsequent reaction.

The means for generating a detection signal based on reaction of said sample fluid may comprise any reagent which will react with a component of the sample fluid and either directly, or indirectly through subsequent reaction, provide a detectable signal indicating the presence of said component. The reagent is preferably selected to provide a quantifiable detection signal which is directly related to the amount of the component of interest in the sample fluid. The reagent may be dispersed in an absorbent material, or preferably, be in the form of a thin film coated upon a carrier film.

The means for separating the receiving means and generating means comprises a plurality of hydrophilic multifilament fibers having a lattice-shaped structure, with the structure having openings defined by adjacent fibers. These openings possess a fiber separation distance which is effective to prevent saturation of the openings by capillary action; typically the separation between fibers ranges between 0.05 and 0.2 mm. The multifilament fibers are preferably woven into a fabric, most preferably into a square-shaped grid.

The means for joining the receiving means and the generating means may be any device which is capable of placing the receiving means and the generating means into fluid contact relationship, such that at least a portion of the sample fluid is transported from the receiving means to the generating means. A preferred embodiment of the joining means comprises a pivot mounting for the generating means which is normally biased away from the receiving means, and which, upon application of mechanical pressure, places the generating means in fluid contact relationship with the receiving means.

The means for supporting the receiving means, the generating means, the separating means and the joining means may be any structure which is capable of supporting them in operative relationship. A plastic planar member upon which the receiving means, separating means, joining means and the generating means are mounted is preferred.

Multi-filament threads comprise a large number of intertwined fibers. Although DE-C-31 30 749 discloses that wool and cotton, which are multifilament materials, are suitable for the hydrophobic net, hydrophobic nets have been manufactured in practice from monofilament threads.

A thread is hydrophilic in the context of the present invention if it absorbs a sample fluid by capillary action and transports it within itself. In doubtful cases hydrophily can easily be determined by a test in which the thread is dipped vertically into an aqueous solution of 7% bovine serum albumin (BSA). With a hydrophobic thread no rise in fluid can be observed, whereas a hydrophilic thread will absorb the fluid up to a capillary height which is characteristic of its hydrophily. Threads of relatively weak hydrophily, having a capillary height of at least 3 mm and not more than approximately 20 mm after one minute in 7% BSA solution, are preferably employed in the practice of the invention.

Another method of testing hydrophily is described in U.S. Pat. No. 4,292,272, which discloses a spreading layer made of fibrous material. The spreading of a drop of a 7% BSA solution on the layer material is used as a criterion. The width of the lattice openings must be sufficient to ensure that the sample fluid does not overcome the gaps between the threads of the separating layer by capillary action. 0.05 mm is accordingly regarded as a minimum lattice width value, a preferred value being approximately 0.1 mm. Excessively large lattice openings are also disadvantageous with respect to both uniformity of color formation and separating effect. The upper limit is approximately 0.2 mm.

The invention will now be explained in detail below with reference to an exemplifying embodiment represented diagrammatically in the Figures.

Although the test carrier 1 shown in FIG. 1 has the overall form of a conventional test strip, it is a high-value analysis system test carrier which is scarcely comparable with known test strips. Other known types of test carriers are for example designed as square platelets provided with a frame, with a test field similar to a photographic slide located in their center. The invention can also be used for test carriers of this kind if a two-step process cycle is desired.

In the test zone 2 of the test carrier 1 several test layers are arranged on base layer 3 of rigid plastic foil. A reservoir layer 4 extends from sample feed zone 5 into a detection zone 6.

In the sample feed zone 5 a pre-reaction layer 7 is disposed above reservoir layer 4 in such a way that it extends above an initial sub-zone 4a of the reservoir layer 4. It is covered by covering net 8, and the layers 4a, 7 and 8 are bonded with hot melt adhesive strip 9 to base layer 3 at their edge facing away from detection zone 6.

In the detection zone 6 a detection layer 11 and a separating layer 12, comprising a lattice of hydrophilic, multifilament fibers separated by a distance "a", are bonded to the base layer, once again with a hot melt adhesive strip 10. The bonding must be carried out at the edge of the layers 11 and 12 which faces away from the sample feed zone 5, in such a way that the latter stand up obliquely from the reservoir layer 4 with the test carrier in its initial state, i.e., before its wetting. In this way the overflow of fluid from the reservoir layer 4 into the detection layer 11 is prevented. Only when flap 13 is pressed downwards, either manually or by means of a device as is described, for example, in U.S. Pat. No. 4,780,283, is fluid contact made between reservoir layer 4 and detection layer 11, and the sample fluid absorbed by the detection layer 11.

This test carrier design with a detection layer separated like a flap is known, for example, from U.S. Pat. No. 4,780,280. In theory, a two-step process cycle is possible with such a carrier design, even without the separating layer 12. Practical experience has shown, however, that premature overflow of fluid from reservoir layer 4 into the detection layer ("early start") cannot be avoided without a separating layer. The present invention is consequently of particular importance in conjunction with such a test carrier. Alternatively, the separating layer and the detection layer can also rest on the reservoir layer when the test carrier is in its initial state, as is disclosed in DE-C-31 30 749.

To perform an analysis, a drop of sample fluid, for example blood, is placed onto the covering net 8, which serves as the sample feeding layer. The pre-reaction layer 7 is preferably designed as an erythrocyte separating layer in order to separate red corpuscles from the blood and provide pure plasma for the analysis. For example, a glass fiber layer as disclosed in U.S. Pat. No. 4,477,575 is suitable. Instead of one pre-reaction layer 7 it is also possible to arrange several layers one on top of the other in the pre-reaction zone, which layers can perform various functions. For example, they may contain reagents which are required in the subsequent course of the analysis.

The sample fluid penetrates from layer 7 into the reservoir layer 4 and is laterally transported in the latter into detection zone 6. Sub-zone 4b of layer 4 forms a fluid reservoir for the subsequent detection reaction, which is initiated by the detection layer and the reservoir layer 4 being pressed against one another perpendicularly to their surfaces.

For high accuracy it is important that a sufficiently large amount of fluid is available in the reservoir layer 4. Since, on the other hand, it is necessary in most cases to work with as small a sample volume as possible, it is advantageous if reservoir layer 4 has a higher suction force for the sample fluid than the layer immediately preceding it in the fluid transport path, so that it substantially empties the layers immediately preceding it. In the context of the present invention it has been established that many materials which exhibit a particularly high suction force have conversely the disadvantage that the liquid is distributed in them non-uniformly. In such cases the distribution effect achieved with the separating layer 12 according to the present invention is of particular importance.

The sample fluid can remain in reservoir layer 4 as long as required for the test procedure. This time can for example be dependent on the completion of an initial reaction stage. It can also be dependent upon attainment of a particular desired temperature. After this the flap 13, comprising layers 11 and 12, is pressed downwards at a fixed point in time. The sample fluid passes into the detection layer 11, so that a second reaction step can take place, during which the detection signal is formed in layer 11.

Figure 2:
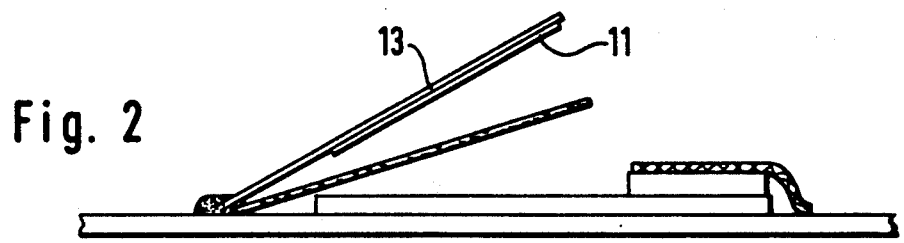
FIG. 2 is a side view of a test carrier according to the invention.

FIG. 2 shows a preferred layout of detection layer 11, comprising a transparent carrier film 13 and a reagent film which is coated as a detection layer 11 onto the surface of the film 13 facing the reservoir layer 4. A reagent film according to U.S. Pat. No. 4,312,834 is particularly suitable, but other films, for example based on gelatin, can also be used. Such detection layers should be as thin as possible, because in this way it is possible to achieve an intensive color formation with small amounts of reagent and sample. The dry detection layer 11 is preferably not more than 0.1 mm, particularly preferably less than 0.05 mm thick. Its fluid absorption per $cm^2$ is preferably less than 8 $\mu l$.

The separating layer 12 should also be thin. Its thickness is preferably below 0.15 mm, particularly preferably below 0.1 mm.

Figure 3:
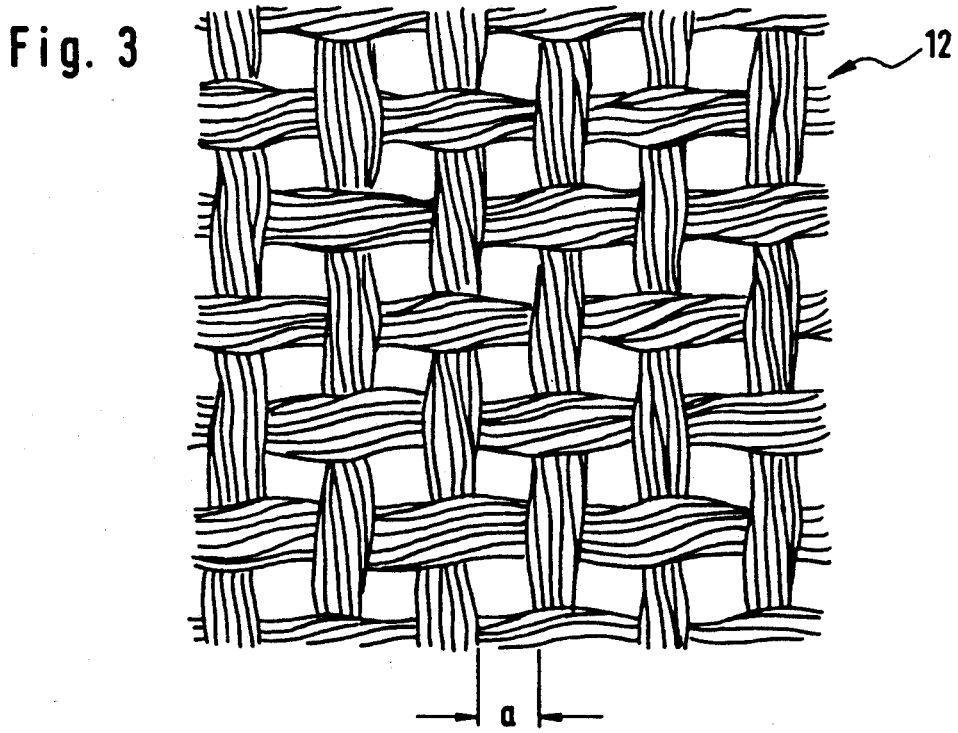
FIG. 3 is a highly magnified top view of a separating layer material suitable for the invention.

FIG. 3 shows clearly the structure of the preferred separating layer 12. The threads comprise a multiplicity of intertwined fibers. They are combined into a lattice-shaped structure (woven in the case shown). The square arrangement shown in the figure, although preferred, is not essential. It is crucial that the width (a) of the grid openings is sufficiently large so that the latter are not saturated with the sample fluid due to capillary action.

EXAMPLE

The Example set forth below is an illustrative species of the generic invention disclosed herein and, as such, further discloses the practice and advantages of the present invention. In no event is this exemplary embodiment intended to limit the allowable scope of the generic invention.

Two different test carriers with the previously described construction were manufactured, which differ only as regards the material used for the separating layer 12.

For test carrier A a monofil nylon fabric "150 HC" from Züricher Beuteltuchfabrik, Zürich, Switzerland, was used. This is a hydrophobic net according to DE-C-31 30 749 consisting of monofilament threads and is used on a large scale for a commercial embodiment of test carriers comprising a separating layer based on this patent.

The separating layer 12 of test carrier B consists of a fabric "PE 14/100 normal" from Schweizer Seidengazefabrik Thal, Switzerland, which is multi-filament and hydrophilic.

In order to determine their hydrophily, the threads of both materials were dipped vertically in a solution of 7% BSA in water. With test carrier A no capillary rise of the fluid on the thread was observed. With test carrier B the fluid rose in 30 sec. to 5 mm and in approximately 45 sec. to 7 mm and remained at this In order to investigate the effect on measurement accuracy, blood samples with ten different, known concentrations of cholesterol were each tested ten times with the test carriers. The results are set out in the following Table:

TABLE

| Cholesterol in the serum (mg/dl) | Hydrophilic Accuracy Test Carrier A | Hydrophilic Accuracy Test Carrier B |
| --- | --- | --- |
| 92 | 3.0 | 1.9 |
| 115 | 2.5 | 1.3 |
| 158 | 6.3 | 1.0 |
| 197 | 3.3 | 2.0 |
| 236 | 2.8 | 2.0 |
| 277 | 1.8 | 1.4 |
| 336 | 2.0 | 1.5 |
| 399 | 2.6 | 2.6 |
| 464 | 1.5 | 2.4 |
| 521 | 1.9 | 1.9 |
| mean accuracy | 2.8 | 1.8 |

The accuracy is given in each case, as is the practice in clinical chemistry, in percent of the variation coefficient (VC).

A clear improvement with the use of the separating layer according to the invention is shown. Separation of the two process steps of the reaction sequence was equally good with both test carriers.

We claim:

1. A test carrier for analyzing a sample fluid with several test layers which form a sample fluid transport path and which contains a reagent system which reacts with the sample fluid to produce a detectable signal, comprising
   a reservoir layer of absorbent material,
   a detection layer, arranged in the fluid transport path downstream of the reservoir layer but separated from fluid contact with said reservoir layer, in which detection layer the detectable signal is formed, and
   a separating layer arranged between the reservoir layer and the detection layer, said separating layer being adapted to prevent sample fluid contact between the reservoir layer and the detection layer until the reservoir layer and the detection layer are pressed against one another, wherein
   the separating layer comprises a lattice-shaped structure, comprising multifilament threads of a hydrophilic material having openings defined by adjacent threads which have a mean width (a) which is greater than 0.05 mm.

2. The test carrier of claim 1, wherein the mean width (a) of the lattice openings is less than 0.2 mm.

3. The test carrier of claim 1, wherein the reservoir layer has a higher suction force for the sample fluid than any test layer arranged before it in the fluid transport path, and wherein said test carrier includes at least one additional test layer of absorbent material in said fluid transport path operatively connected to said reservoir layer in a manner adapted to empty fluid from said additional test layer by suction.

4. The test carrier of claim 1, wherein the detection layer has a maximum thickness of 0.1 mm.

5. The test carrier of claim 1, wherein the detection layer has a maximum fluid absorption volume of 8 $\mu$l per $cm^2$.

6. The test carrier of claim 1, wherein the thickness of the separating layer is not more than approximately 0.15 mm.

7. A test carrier for analysis of a sample fluid, adapted to determine the concentration of an analyte therein, comprising:
   i) means for receiving and storing a sample fluid;
   ii) reagent means adapted to react with said sample fluid to generate a detectable signal indicative of said analyte in said sample fluid;
   wherein said means for receiving said sample fluid and said reagent means are initially separated from fluid contact;
   iii) separator means disposed between said receiving means and said reacting means, comprising a lattice-shaped structure comprising a plurality of hydrophilic multifilament fibers defining openings between adjacent intersecting fibers, and said openings having a fiber separation distance which is effective to prevent saturation of the openings by said sample fluid by capillary action;
   iv) means for joining said receiving means and said reagent means into fluid contact relationship thereby transporting at least a portion of said sample fluid from said receiving means into reacting relationship with said reagent means to generate a detectable signal; and
   v) means for supporting said receiving means, said reagent means, said separator means and said joining means.

8. A process for the determination of an analyte in a sample fluid, comprising
   depositing a sample fluid on a sample fluid reservoir area of a test carrier,
   providing a signal generation area containing a reagent capable of reacting with said analyte, which is initially separated from fluid contact relationship with said reservoir area,
   providing a separator comprising a lattice-shaped plurality of hydrophilic multifilament fibers, having openings defined by adjacent fibers, having a fiber separation distance which is effective to prevent saturation of said openings by said sample fluid by capillary action, located between said reservoir area and said signal generation area, which is not initially in fluid contact relationship with said reservoir area,
   placing said signal generation area into fluid contact relationship with said reservoir area through said separator,
   reacting said analyte in said sample fluid with said reagent in said signal generation area to produce a detectable signal, and
   measuring said detectable signal.

9. The process of claim 8 wherein the reaction between said analyte and said reagent occurs at a temperature between 5° C. above the freezing temperature of said sample fluid and 5° below the boiling temperature of said sample fluid.

10. The process of claim 9 wherein said reaction occurs at ambient temperature.

11. The process of claim 8, further comprising, prior to reacting said analyte with said reagent, initially removing a component of the sample fluid other than said analyte, then, placing said signal generation area into fluid contact relationship with said reservoir area.

12. The process of claim 8, wherein said analyte is cholesterol and said sample fluid is blood serum.

* * * * *